US006296652B1

(12) United States Patent
Qingmin

(10) Patent No.: US 6,296,652 B1
(45) Date of Patent: Oct. 2, 2001

(54) DRUG-WITHDRAWAL-SYNDROME AURICLE-THERAPEUTIC DEVICE

(76) Inventor: Wu Qingmin, Room 102, Flat 4, 17# Huaxin Xiang, Nanjing, Jiangsu Province (CN)

( * ) Notice: Subject to any disclaimer, the term of this patent is extended or adjusted under 35 U.S.C. 154(b) by 0 days.

(21) Appl. No.: 09/320,242

(22) Filed: May 26, 1999

(30) Foreign Application Priority Data

May 26, 1998 (CN) ........................ 98111321

(51) Int. Cl.[7] ........................ A61B 17/34
(52) U.S. Cl. ........................ 606/189
(58) Field of Search ........................ 606/188, 189, 606/204

(56) References Cited

U.S. PATENT DOCUMENTS

| | | | | |
|---|---|---|---|---|
| 3,938,526 | * | 2/1976 | Anderson et al. | 128/303 |
| 4,915,110 | * | 4/1990 | Kitov | 128/783 |
| 4,940,060 | * | 7/1990 | Gu et al. | 128/735 |

FOREIGN PATENT DOCUMENTS

| | | |
|---|---|---|
| 88109290.8 | 8/1989 | (CN) . |
| 93207564.9 | 1/1994 | (CN) . |
| 94107366.1 | 4/1995 | (CN) . |
| 95116455.4 | 9/1996 | (CN) . |
| 98111321.4 | 1/1999 | (CN) . |
| 98226129.2 | 7/1999 | (CN) . |

* cited by examiner

*Primary Examiner*—Cary E. O'Connor
(74) *Attorney, Agent, or Firm*—Knobbe, Martens, Olson & Bear, LLP

(57) ABSTRACT

A device for treating the undesirable symptoms resulting from cessation of habitual drug use, which can include insomnia, anxiety, tremors, loss of appetite, drowsiness, nausea, and sweating, and for reducing the rate of recurrence of drug use following treatment through the use of a programmed series of acupuncture, massage, and/or moxibustion treatments of acupuncture points in a subject's ear(s). The device includes a housing that conforms to the contour of a human ear containing a plurality of acupuncture needles held in an elastomeric structure and connected to a movable elongate member such that the plurality of needles may be brought into intermittent contact with the inner surface of the ear with an approximately equal force. The device further includes a control circuit adapted to automatically control the application of acupuncture stimulating current, moxibustion, and/or massage in a programmable manner. The device allows a user to program a treatment regimen into the device, removably affix the device adjacent at least one of a subject's ears, and provide the programmed acupuncture, moxibustion, and/or massage treatments to a plurality of known acupuncture points on the inner surface of the subject's ear(s). In one embodiment, the acupuncture needles are made of a permanently magnetic material to include an auxiliary magnetic treatment. In an alternative embodiment, the device also includes a vocal and/or musical sound generating component as additional therapy.

8 Claims, 7 Drawing Sheets

"LCD DISPLAY UNIT"

DRUG-WITHDRAWAL-SYNDROME AURICLE-THERAPEUTIC DEVICE

FIELD OF THE INVENTION

The invention concerns a therapeutic device, particularly, a therapeutic device for treating drug withdrawal syndrome.

BACKGROUND OF THE INVENTION

What is called drug withdrawal syndrome means such serious syndrome as being anger for drug, anxiety, frequently giving yawn, sweating, running with tears, running nose, drowsing, dilated pupil, being goose flesh, tremor, shivering, muscle aching, headache, losing appetite, insomnia, even blood pressure rising, frequency and depth of breath increasing, pulse quickening, restless, nausea, curling, vomiting, diarrhea, spermatorrhea, etc. occurred after stopping drug-taking.

Chemotherapy of entire course integrated the three phases addiction-removing, consolidation and rehabilitation is adopted in drug-giving-up treatment now. Body acupuncture and ear acupuncture therapies by hand-needling or electroimpulse output only are used for an auxiliary means. Modern drug-giving-up therapy is a pure chemotherapy. Addiction-removing therapy taking opium acceptor analeptic such as methadone, opium, dihydroetorphine and others or opium acceptor partial analeptic—buprenorphine as alternatives, or addiction-removing taking non-opium clonidine, existing preserving treatment taking naltrexone or methadone in consolidation therapy. The above-mentioned therapies, generally speaking, have many advantages such as reliable efficiency, fast addiction-removing action and relative safety. While there exist problems with them. These include more undesirable reaction, heavier toxic side effects, undetermined effect in giving up abuse of many drugs due to addiction to narcotic drug, trend of some medicines producing dependence, consequently treating medicines having been turned new narcotic drugs and leading new addiction to them. After addiction-removed by modern drug-giving-up treatment, some procrastinated withdrawal syndromes still exists at different extents with sufferers, even though taking naltrexone to consolidate effect, 90~95% drug-retaking rate still occurs during six months after addiction-removing treatment using different giving-up medicines in modern drug-giving-up therapy, in result, the vicious circle of habituation—addiction-removing—Addiction-recovering—addiction-re-removing almost can not be broken. The existing acupuncture or ear acupuncture therapy and electronics designed based the principle of science of acupuncture and moxibustion is a pure physical therapy, and is only used as an auxiliary means. Hand-needling treatment is not easy to master exactly and may cause pain and infection due to improper operation. Drug-giving-up effect may be unsatisfactory and unsteady when design of the devices is unreasonable, or the devices are not convenient to use due to their low automatic degree. Consequently, popularization of the treatment method in the drug-giving-up field is blocked.

Purpose of the invention is to resolve the problems above, and provides a drug-giving-up-syndrome auricle-therapeutic device having features such as safety, painless, no toxic and side effect, no addictive effect, low drug-retaking rate and better curative effect.

SUMMARY OF THE INVENTION

A therapeutic device for auricle treating syndrome during drug giving-up consists of an ear point-treating unit and controller. The controller contains CPU, data memory, control logic circuit and LC display. The feature of the therapeutic device is as fellows:

a. The ear point-treating unit consists of an ear-like frame, point electrode needles, electrode needle control mechanism and housing. The ear-like frame is a solid body profiling human ear. On the frame are made many through-going holes at those locations corresponding to standard points of human ear. In the holes are respective electric needles, which leads are connected to controller outside the housing. The ear-like frame is connected in the front of housing and protrudes beyond its front. There is electrode needle control mechanism consisting of elastomer, vibrating head, push rod, spring etc. at the rear opposite to the ear-like frame in the housing.

b. I/O terminals of CPU of the controller connect impulse output circuit and massage/acupuncture and moxibustion commutation logic circuit. Output of impulse output circuit is sent different point electrode needles and vibrating heads via output transformer. Output of commutation logic circuit synchronously controls output states of impulse output circuit and the secondary of the output transformer, to selectively control output is for electrode needle treating or vibrating head treating.

The invention contains an ear point-treating unit and controller. On one hand, it can avoid defects of chemotherapy including heavier negative effect, treatment in phases, higher drug-retaking rate after giving-up, to realizes the purpose to integrate addiction-removing, consolidation and rehabilitation as an entire course of treatment with advantages such as safe use, no toxic and side effect, no addictive effect, reduced drug-retaking rate. On other hand, the invention can eliminate inadequacy of manual operation in physical therapy in larger arbitrariness, wound pain, easy infection, inconvenience and unreasonable design of the existing devices, and realize design-reasonable, advanced, higher-automatic, non-intervening, painless, fast-effective and exactly efficient treatment. Besides, the invention has the following features:

1. Complete: means the device is suitable for entire course of treatment. It may not only be used for drug withdrawal syndrome, also for procrastinated giving-up-syndromes, and consolidation and rehabilitation as well. In addition, it is also applicable to other withdrawal syndromes caused by smoking, liquor drinking or other medicine taking.
2. Exact: means that the treating head of device adopts an ear point-treating unit in order to position ear points exactly, reliably contact auricle skin and use for positioning treatment on auricles of different profiles.
3. Good: i.e. good treating effect. When converter electroimpulse as output of control device and magnetic compound electrode of treating head act on special serious of points for treating giving-up-syndrome on auricle corresponding to shenmen point, renicapsule, heart, lung, subcortex, brain, incretion, kidney and other, the device may produce highly centralized effect combining electrotherapy, magnet therapy, acupuncture, massage, music therapy, audio and video effect to implement psychological therapy and physical therapy synchronously, continuously weaken positively strengthening effect of drug, rapidly rid negatively strengthening effect, and attenuate psychological eagerness and pain due to withdrawal syndrome, so reduce drug-retaking rate.

4. Not: means that the therapy using the device is a painless pure physical, safe and economic one without toxic and side effect, belongs to natural therapy category.
5. Convenient: i.e. what requires sufferer to do only is to switch power supply on, and slightly adjust current output as prompted by the device, treating operation is automatically implemented by the device thanks to its higher automatic control degree.
6. Wide: means that the device may be used for treatment of other diseases based the principle of the invention when electrode needles are regulated to positions of corresponding to points on auricle.

Figure 1:
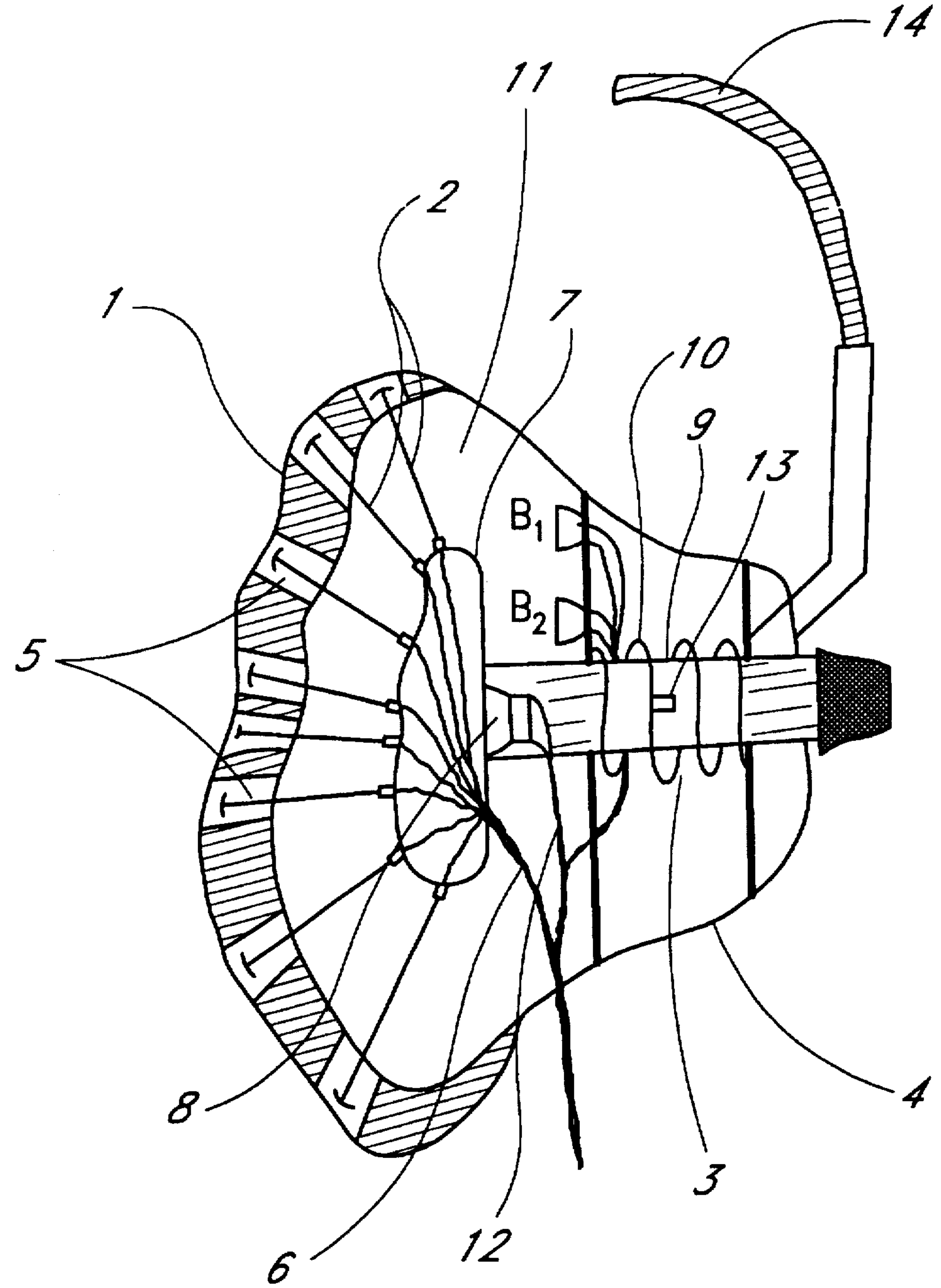
FIG. 1 is a scheme of ear point-treating unit in the invention.
Figure 2:
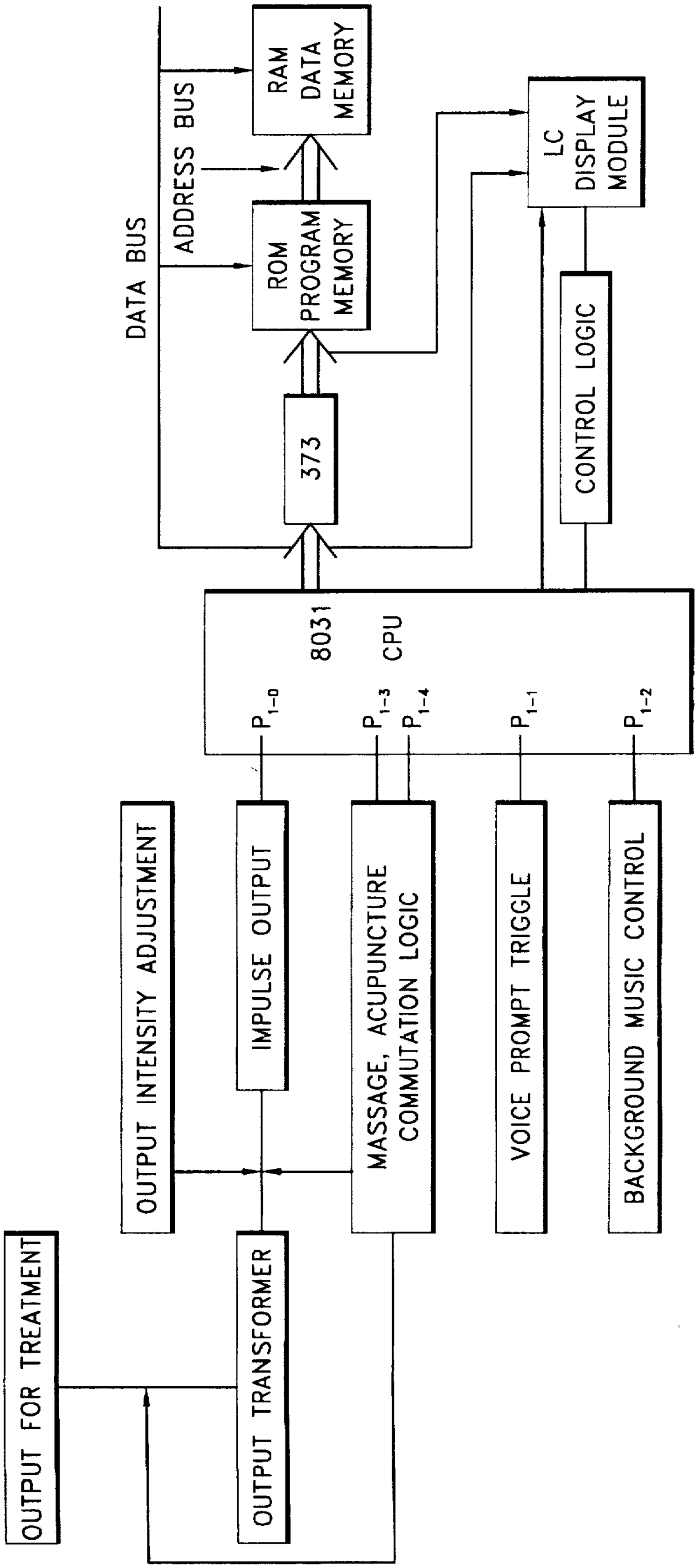
FIG. 2 shows a functional-block diagram of the controller in the invention.

As illustrated in FIGS. 1 and 2, the device of the invention consists of ear point-treating unit and controller. Of them, the ear point-treating unit consists of an ear-like frame 1, point electrode needles 2, electrode needle control mechanism 3 and housing 4. The ear-like frame 1 is a solid body profiling human ear. On the frame are made many through-going holes 5 at those locations corresponding to standard points of human ear. In the holes 5 are respective electric needles 2, which leads 6 are connected to controller outside the housing 4. The ear-like frame 1 is connected in the front of housing 4 and protrudes beyond its front. There is electrode needle control mechanism 3 consisting of elastomer 7, vibrating head 8, push rod 9, spring 10 at the rear opposite to the ear-like frame 1 in the housing 4. That elastomer 7 (soft rubber or plastics and so on) abovementioned is located within a bow cavity 11 behind the ear-like frame 1. Profile of elastomer 7 is fit the bow cavity 11, its front bow face is against the rear end of corresponding point electrode needles 2 in the holes 5 of the ear-like frame 1. The vibrating head 8 and the push rod 9 connect the rear of elastomer 7. Of them, the lead 12 of vibrating head 8 is outward the housing 4 to connect the controller. The external end of push rod 9 protrudes outside of the rear of housing 4 and is splited by spring 10 on it. There is a spring-loaded lock tab 13 on the push rod 9. Profile of the bow cavity 11 behind the ear-like frame 1 is preferably same as the protruding face on its front matching that of human ear, so that the front bow face of elastomer 7 is suitable to human ear to ensure equal active force elastomer 7 exerted on respective point electrode needles 2. The controller of the invention includes CPU, data memory, control logic circuit and LC display. Feature of the invention is I/O terminals of CPU of the controller connect impulse output circuit and massage/acupuncture and moxibustion commutation logic circuit. Output of impulse output circuit is sent different point electrode needles and vibrating heads via output transformer. Output of commutation logic circuit synchronously controls output states of impulse output circuit and the secondary of the output transformer, to selectively control output is for electrode needle treating or vibrating head treating. On I/O terminals of CPU have voice prompting circuit and background music circuit connected to give auxiliary treatment.

Figure 3:
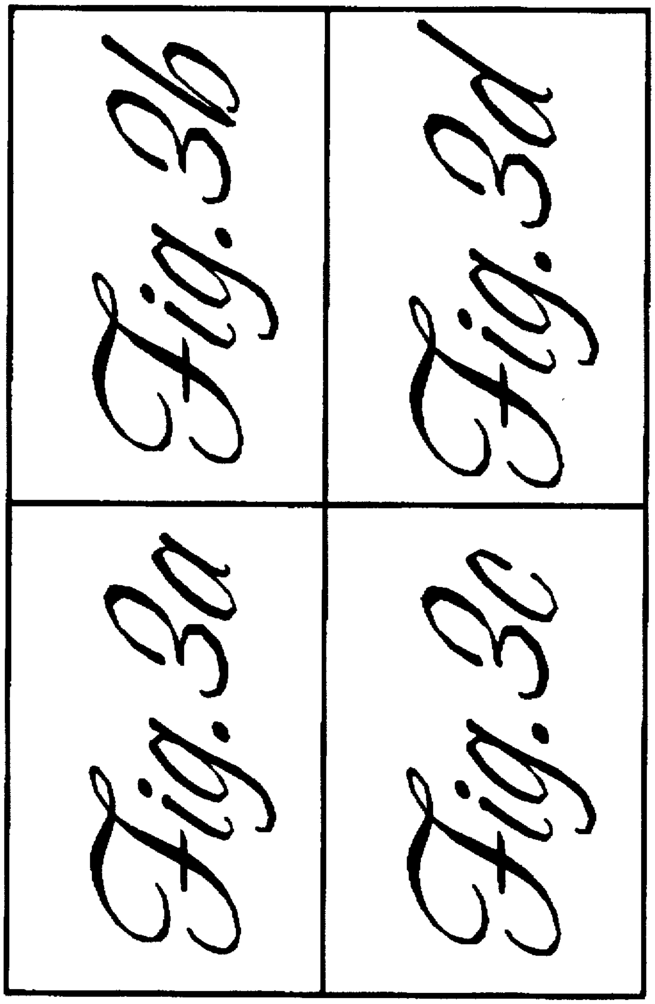
FIG. 3 illustrates electrical principle of practical example of the controller in the invention.
Figure 3A:
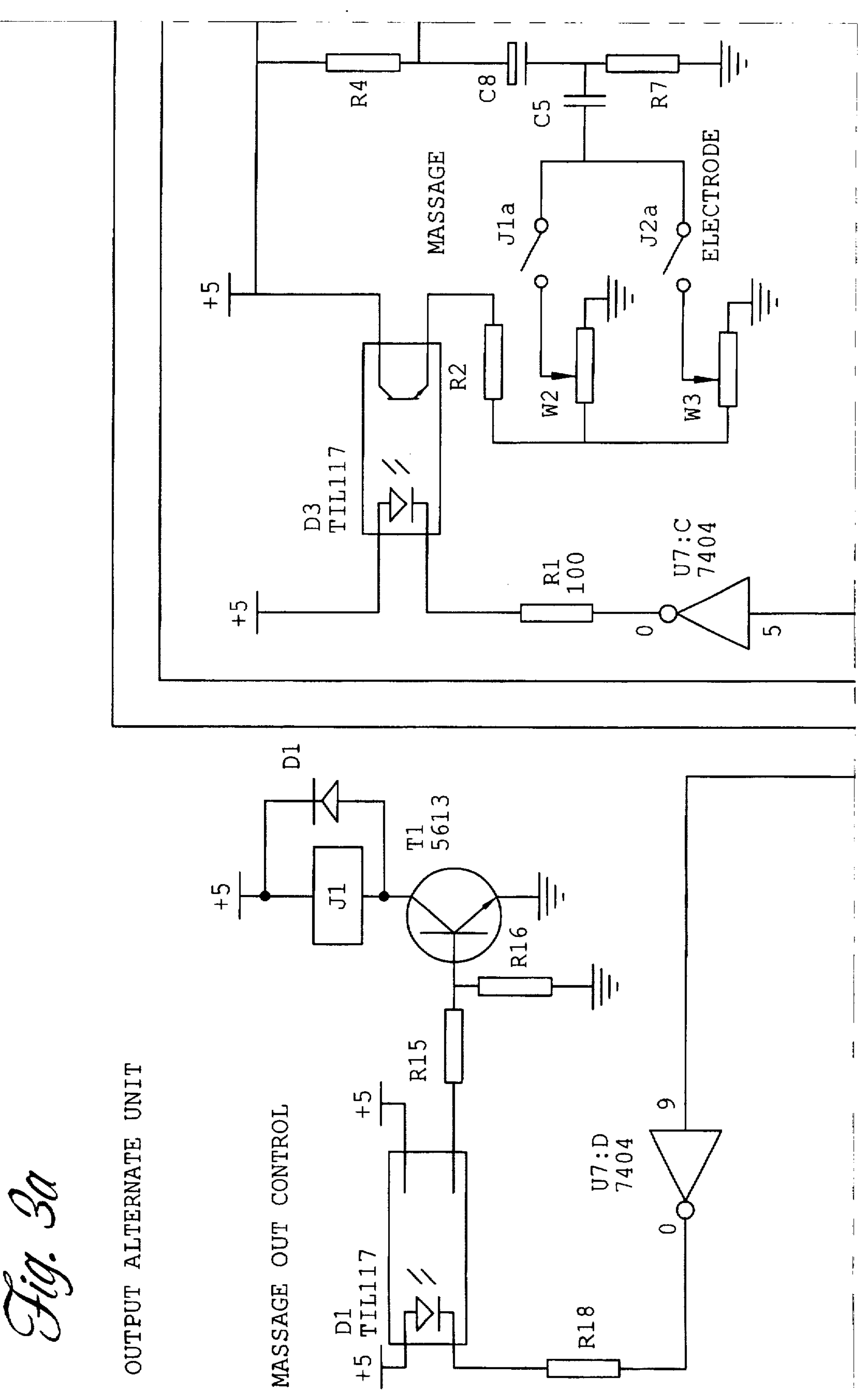
Figure 3B:
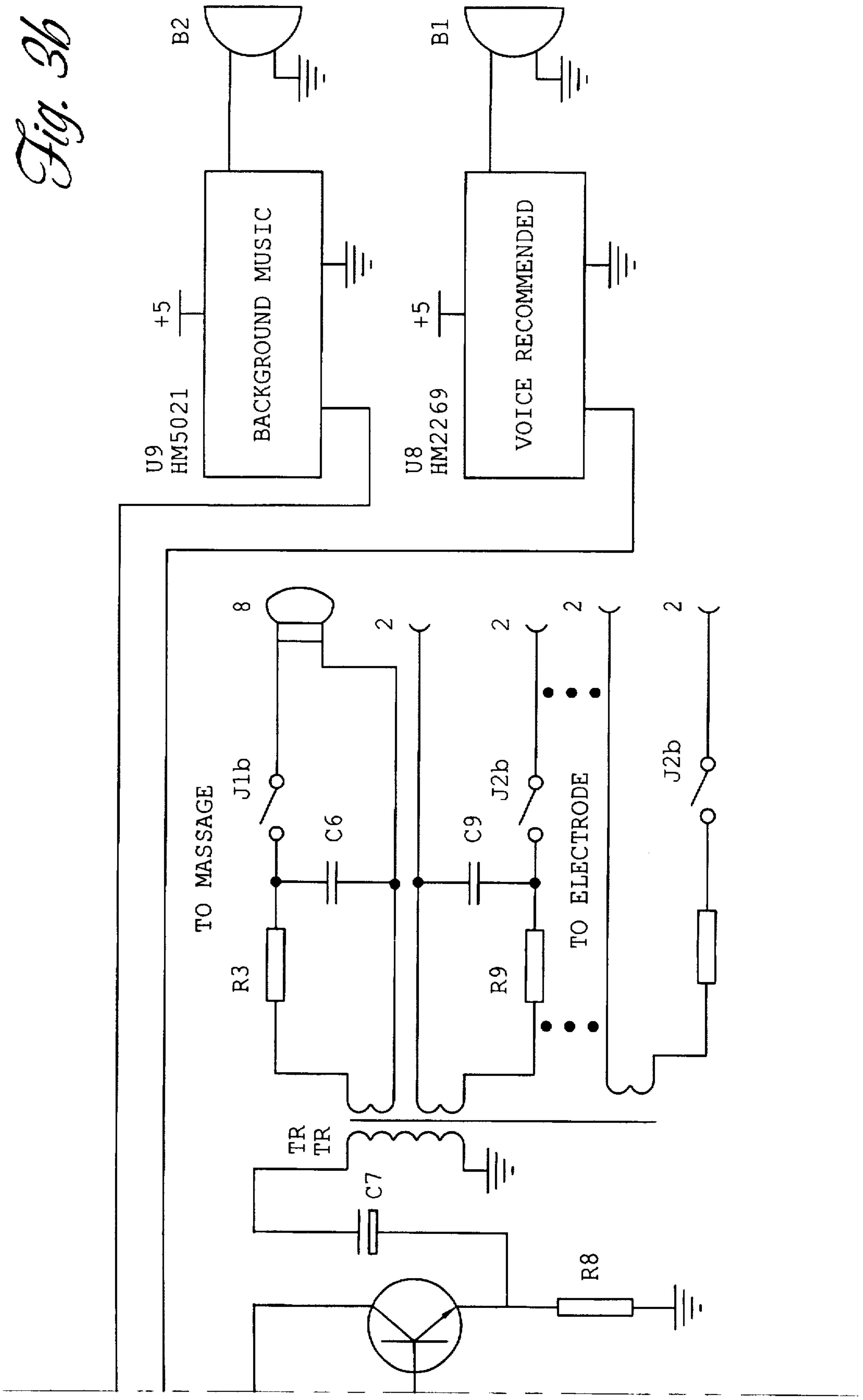
Figure 3C:
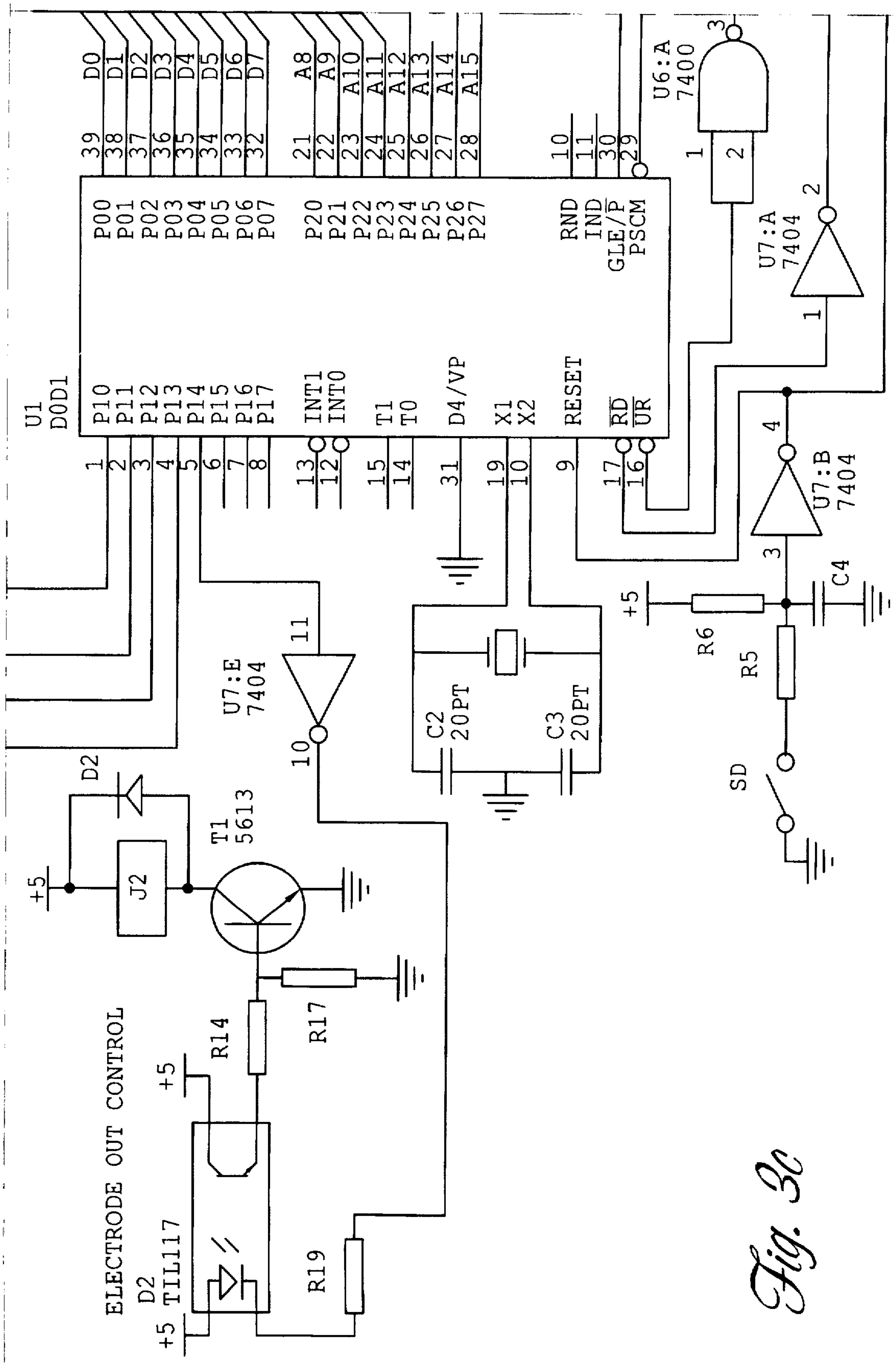
Figure 3D:
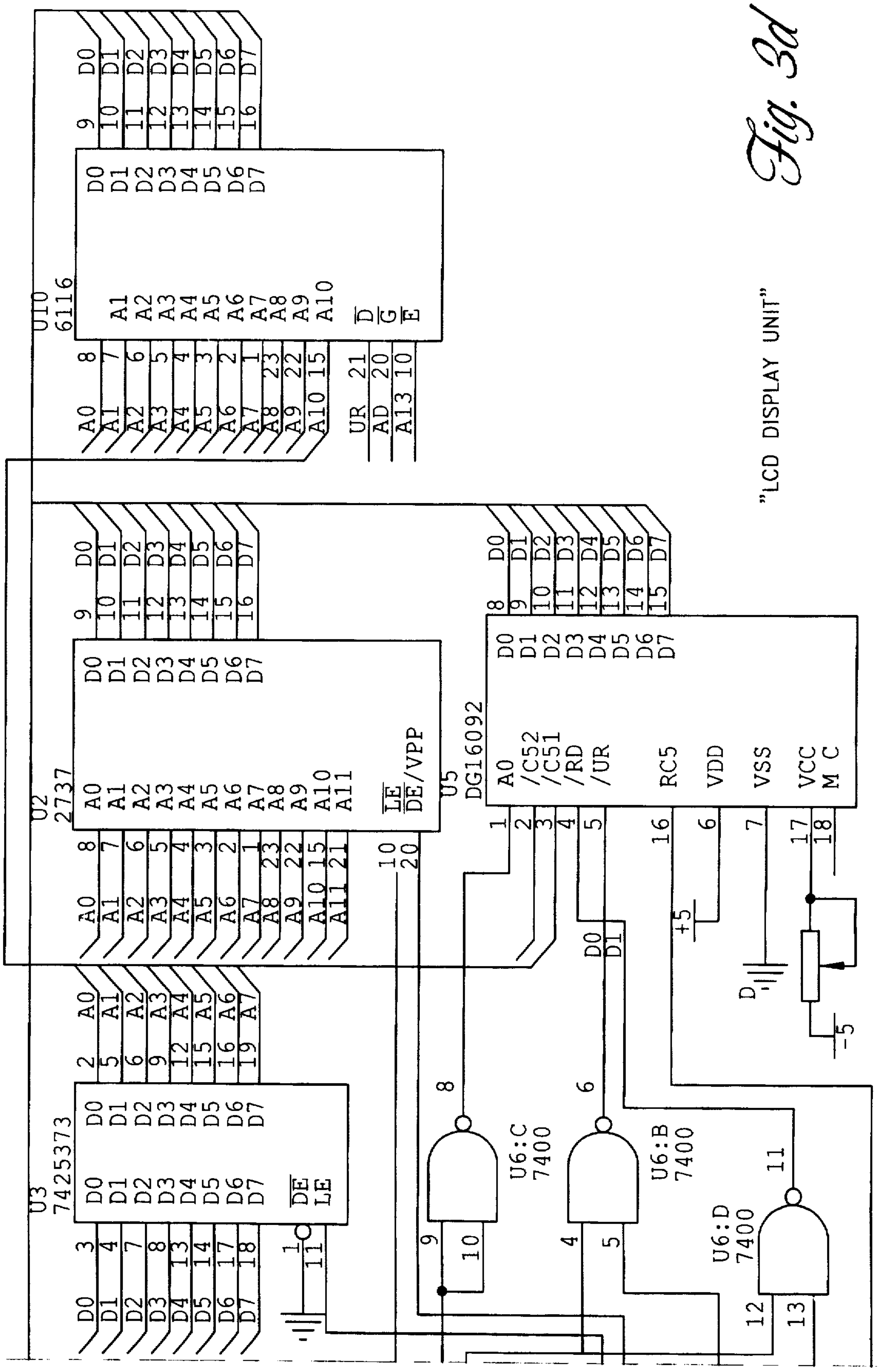

A practical example of the controller in the invention is as shown in FIG. 3. It contains CPU U1 (for example 8031) and its address latch U3 (for example Model 373, program memory U2 (for example Model 2732), data memory U10 (for example Model 6116), control logic circuit (consisting of NAND gate U6A–U6D and inverter U7A) and LC display U5 (for example Model DG16032). Control logic circuit is used to match CPU U1 with LC display U5. Impulse output circuit in the invention consists of photoelectric coupled circuit, commutation circuit, differential circuit, and emitter-follower. The photoelectric coupler circuit consists of inverter U7C, resistor R1, photo coupler O3. The commutation circuit consists of resistor R2, potentiometers W2, W3, and N.O. contacts J1*a*, J2*a* of relays J1, J2. The differential circuit consists of capacitor C5 and resistor R7. The emitter-follower circuit consists of transistor T, resistors R4, R8, capacitors C7, C8. Input of inverter U7C in photoelectric coupled circuit is connected corresponding I/O terminals of CPU U1. Output of U7C is connected input of photo coupler O3 via resistor R1, output of photo coupler O3 connects one terminal of paralleled two potentiometers W2, W3 in commutation circuit via resistor R2, another terminal of W2 and W3 is grounded. Intermediate adjusting terminals of W2, W3, via N.O. contacts J1*a*, J2*a* of relays J1, J2, respectively, connect input of differential circuit, i.e. a terminal of capacitor C5. Output of differential circuit runs from connecting point of capacitor C5 and resistor R7 to base input of emitter-follower T. Emitter output terminal of T connects primary coil of transformer TR. Secondary coil of TR has multiple winding outputs. Of them, a winding connects vibrating head 8 via N.O. contact J1*b* of relay J1; the others are connected respective electrode needles 2 via N.O. contact J2*b* of relay J2. Massage/acupuncture and moxibustion commutation logic circuit of the invention consists of inverters U7D, U7E, photo couplers O1, O2, transistors T1, T2, relays J1, J2, diodes D1, D2, resistors R14–R19. Of them, Inputs of inverters U7D, U7E connect corresponding I/O terminals of CPU U1, respectively, Outputs of U7D and U7E connect their respective photo couplers O1, O2 via resistors R18, R19, respectively. Outputs of O1 and O2 connect base inputs of their respective transistors T1, T2 via resistors R15, R14, respectively. Collector outputs of T1, T2 connect their respective relays J1, J2. J1 and J2 synchronously control working state of commutation circuit in impulse output circuit and output state of the secondary of output transformer TR by their N.O. contacts J1*a*, J2*a*, J1*b*, J2*b*. I/O terminals of CPU U1 in the invention connect respective horns B1, B2 via voice integrated circuit block U8 (for example Model HM2269) and music integrated circuit block (for example Model HM5021) to implement auxiliary treatment.

Either a single or a couple of ear point-treating unit(s) of the invention may be used. When a couple of the units are used, they are placed in left and right ears, respectively, and linked together with an ear-clamp 14 like that used on earphone. After they are placed in someone's ears, they will snuggle up to surfaces of ears since the profile of ear-like frame 1 is matched that of human ear. Now push the push rod 9, make it to compress spring 10 and drive elastomer 7 to move forward, respective pairs of electrode needles 2 will run forward through holes 5 on the ear-like frame 1 and pressed on a serious of special points for treating withdrawal syndrome on sufferer's ears. These point electrode needles 2 may be made of magnetic needles, which tip may be formed different special geometric shapes and coated by a conductive material with antianaphylaxis. Then open spring-loaded lock tab 13 to lock spring 10, so fix push rod 9, elastomer 7 and position point electrode needles 2 at points for treating withdrawal syndrome. At the moment, switch power supply on to start treating process. CPU U 1 controls output state of massage/acupuncture and moxibustion commutation logic circuit under control of software as setting requirement. U1 also controls work of impulse output circuit to output a converter electroimpulse such as continuous wave, spacing wave, or variable-density wave, and make vibrating head 8 or electrode needles 2 to work by output transformer. When massage treatment is required, inverter U7D, photo coupler O1, and transistor T1 start operation to make relay J1 to pick up. I.e. its N.O. contacts J1*a* and J1*b* are closed, potentiometer W2 in commutation circuit of impulse output circuit and vibrating head 8 continued on the secondary of output transformer TR is in On state, massage current may be changed by adjusting resistance of W2. Now vibrating head 8 is working, it vibrates at the output frequency and brings linked elastomer 7 in ear point-treating unit to vibrate together, so then elastomer 7 drives respective electrode needles 2 to massage and stimulate corresponding points, finishing a process of massage treatment. When acupuncture and maxibustion treatment is required, inverter U7E, photo coupler O2, and transistor T2 in massage/acupuncture and maxibustion commutation logic circuit start operation to make relay J2 to pick up. I.e. it N.O. contacts J2*a* and J2*b* are closed, potentiometer W3 in commutation circuit of impulse output circuit and respective group of point electrode needles 2 continued on the secondary of output transformer TR is in On state, acupuncture current may be changed by adjusting resistance of W3. Now respective pairs of electrode needles form their own loops and make electrostimulation on corresponding points at output frequency and current intensity, finishing a process of acupuncture treatment like massage. During the device of the invention is working, controller makes CPU U1 to drive voice integrated circuit block U8 and music integrated circuit block U9 to operation by control of program. So horn B1 and B2 will give special music and intermittent voice synchronously outputted during entire treating process to prompt output of different functions. Any sufferer may adjust output current intensity by means of voice prompt and the showed on LC display, to reach most suitable degree in tingle, numb, pungent, hot, ache feeling for himself or herself. The device of the invention is equipped with selector switch for left or right ear, normally, treatment shall be alternatively done on both, on one ear first, then on the other one.

The treatment mechanism used by the invention is that information output of the device is sent to a particular position of brain axis via an existing holographic reflect link (i.e. the holographic chain of nerve cell in nerve center). When reticular cells structure of brain axis is common excited, a number of pulses from incoming nerve fiber are smoothly sent higher nerve center via reticular structure. They can inhibit or block excitation and discharging occurred in such areas as brain locus caeruleus core due to withdrawal syndrome, reduce potential in these areas to eliminate physiologically and psychologically withdrawal syndrome caused by disinhibition of NE and excess movement. Holographic peculiar effect, holographic phase effect and holographic extensive effect, which are produced by output of information, promote nervous centralis to relieve different types of opium peptides and enhance affinity of the later with opium acceptor by triggering and improving positive and negative feedback system in higher nervous center, and weakening and eliminating negative feedback inhibition of endogenous opium peptide. After returned to normal level, endogenous opium peptide further adjusts a serious of nervous and body fluid immunity system to keep normal internal function balance by a system composed of opium acceptor and opium peptide. In the way, the device will give sufferers release from pain from withdrawal syndrome, remove their physiological and psychological dependence, besides, the device is also used for treatment of other diseases.

What is claimed is:

1. A drug-withdrawal-syndrome auricle-therapeutic device comprising:
   - a controller including a CPU having I/O terminals, a data memory, a control logic circuit, and a display;
   - an ear acupressure point-treating unit, wherein the ear acupressure point-treating unit includes an ear-like frame, a plurality of acupressure point electrode needles, an electrode needle control mechanism, and a housing, the ear-like frame having a solid body profiling a human ear with a plurality of through-going holes at locations corresponding to standard acupressure points of a human ear, the electrode needles extending through the holes to thereby be automatically positioned adjacent the standard acupressure points so as to provide therapeutic acupressure current to the acupressure points selectively provided by the controller, a first end of the electrode needles being electrically connected to the controller which is located outside the housing, the ear-like frame being connected to a first end of the housing and protruding beyond the first end of the housing;
   - a voice prompting circuit and a background music circuit connected to the CPU via the I/O terminals to provide auxiliary auditory treatment via included sound generating devices; and
   - an electrode needle control mechanism including an elastomer, a vibrating head, a push rod, and a spring, the electrode needle control mechanism being located at a second end of the housing, opposite to the ear-like frame wherein the I/O terminals of the CPU of the controller are connected to an impulse output circuit and a circuit for providing at least one of a massage, acupressure, auditory, or moxibustion treatment, commutation logic circuit, an output of the impulse output circuit being connected to pairs of different point electrode needles and the vibrating head via an output transformer, an output of a switching logic circuit synchronously controlling the output of the impulse output circuit and of the secondary output of the transformer in order to select a treatment mode for at least one of the electrode needle pairs and the vibrating head, wherein the device provides a programmable sequence of at least one of an acupressure, massage, auditory, or moxibustion treatment to at least one pair of acupressure points located on the inner surface of at least one of a subject's ears.

2. The drug-withdrawal-syndrome auricle-therapeutic device of claim 1, wherein the at least one pair of acupressure points comprises corresponding points located on opposite ears.

3. The drug-withdrawal-syndrome auricle-therapeutic device of claim 2, wherein the elastomer in said control mechanism of the electrode needles is located within a cavity within the ear-like frame, the elastomer having a profile which corresponds with the cavity, the elastomer having a first face which secures a first end of corresponding point electrode needles in the through-going holes of the ear-like frame, the vibrating head and a first end of the push rod being connected to a second face of said elastomer opposite the first face, wherein the lead of the vibrating head extends out of the housing to connect to the controller, and wherein a second end of the push rod protrudes outside of the rear of the housing with a spring resiliently urging the push rod toward the elastomer.

4. The drug-withdrawal-syndrome auricle-therapeutic device of claim 3, wherein the cavity within the ear-like frame has a profile which has a protruding first face which corresponds to the shape of a front face of a human ear, so that the first face of the elastomer conforms to a human ear to ensure that the elastomer exerts an approximately equal load force on the first ends of respective point electrode needles to thereby cause second ends of the point electrode needles to bear on a subject's ear(s) with an approximately equal load force.

5. The drug-withdrawal-syndrome auricle-therapeutic device of claim 2, wherein the impulse output circuit comprises a photoelectric coupled circuit, a switching circuit, a differential circuit, and an emitter-follower, the photoelectric coupler circuit including inverter U7C, resistor R1 and photo coupler O3, the switching circuit including resistor R2, potentiometers W2, W3 and normally open contacts J1*a*, J2*a* of relays J1, J2, the differential circuit including capacitor C5 and resistor R7, the emitter-follower circuit including transistor T, resistors R4, R8 and capacitors C7, C8, an input of inverter U7C in the photoelectric coupled circuit being connected to corresponding I/O terminals of the CPU, an output of inverter U7C being connected to an input of photo coupler O3 via resistor R1, an output of the photo coupler O3 being connected to a terminal of two paralleled potentiometers W2, W3 in the switching circuit via resistor R2, with another terminal of W1 and W2 being grounded, with intermediate adjusting terminals of W2, W3 via normally open contacts J1*a*, J2*a* of relays J1, J2 respectively, being connected to an input of the differential circuit through a terminal of capacitor C5, and with an output of the differential circuit running from a node of capacitor C5 and resistor R7 to a base input of emitter-follower T, and with an output terminal of emitter-follower T being connected to a primary coil of transformer TR, the secondary coil of transformer TR having multiple winding outputs one of which is connected to the vibrating head via normally open contact J1*b* of relay J1; and with the other(s) winding outputs being connected to the respective electrode needles via normally open contact J2*b* of relay J2.

6. The drug-withdrawal-syndrome auricle-therapeutic device of claim 2, wherein the massage, acupressure, auditory, and moxibustion switching logic circuit further comprises inverters U7D, U7E, photo couplers O1, O2, transistors T1, T2, relays J1, J2, diodes D1, D2 and resistors R14–R19, and wherein inputs of inverters U7D, U7E are connected to corresponding I/O terminals of CPU U1, respectively, with outputs of the inverters being connected to their respective inputs of photo couplers O1, O2 via resistors R18, R19, respectively, and with outputs of O1 and O2 being connected to base inputs of their respective transistors T1, T2 via resistors R15, R14, respectively, and with collector outputs of T1, T2 connecting their respective relays J1, J2, respectively, wherein relays J1 and J2 synchronously control a working state of the switching circuit in the impulse output circuit and output state of the secondary output of transformer TR by the normally open contacts J1*a*, J2*a*, J1*b*, J2*b*.

7. The drug-withdrawal-syndrome auricle-therapeutic device of claim 2, wherein the I/O terminals of the CPU are connected to respective speakers B1, B2 via a voice integrated circuit block U8 and a music integrated circuit block U9 to implement auxiliary vocal and music treatment.

8. The drug-withdrawal-syndrome auricle-therapeutic device of claim 2, wherein the point electrode needles are made of magnetic needles, the needles having tips coated by a conductive antianaphylactic material.

* * * * *